United States Patent [19]

Edwards et al.

[11] Patent Number: 5,413,788

[45] Date of Patent: * May 9, 1995

[54] ANTIMICROBIAL COMPOSITIONS

[75] Inventors: Neil Edwards, Reading; Stephen B. Mitchell, Cardiff; Allin S. Pratt, Oxon, all of United Kingdom

[73] Assignee: Johnson Matthey Public Limited Company, London, England

[ * ] Notice: The portion of the term of this patent subsequent to Mar. 6, 2007 has been disclaimed.

[21] Appl. No.: 425,221

[22] Filed: Oct. 19, 1989

Related U.S. Application Data

[63] Continuation-in-part of Ser. No. 68,365, Jul. 1, 1987, Pat. No. 4,906,466.

[30] Foreign Application Priority Data

Jul. 3, 1986 [GB] United Kingdom ................ 8616294

[51] Int. Cl.⁶ ...................... A61K 6/08; A61K 31/74
[52] U.S. Cl. ..................... 424/409; 424/617; 424/618; 424/421
[58] Field of Search ............... 424/78, 421, 132, 618, 424/617, 409

[56] References Cited

U.S. PATENT DOCUMENTS

| | | | |
|---|---|---|---|
| 2,066,271 | 7/1936 | Irwin | 424/619 |
| 2,595,290 | 5/1952 | Quinn | 424/419 |
| 3,137,618 | 6/1964 | Pearce | 424/421 |
| 4,144,050 | 3/1979 | Frensch et al. | 71/120 |
| 4,608,247 | 8/1986 | Heinig, Jr. | 424/421 |
| 4,849,223 | 7/1989 | Pratt et al. | 424/409 |
| 4,906,466 | 3/1990 | Edwards et al. | 424/421 |

FOREIGN PATENT DOCUMENTS

| | | | |
|---|---|---|---|
| 0116865 | 8/1984 | European Pat. Off. | |
| 0190504 | 8/1986 | European Pat. Off. | A01N 59/16 |
| 644087 | 7/1984 | Switzerland | A01N 59/16 |

*Primary Examiner*—Therman K. Page
*Assistant Examiner*—Peter F. Kulkosky
*Attorney, Agent, or Firm*—Cushman, Darby & Cushman

[57] ABSTRACT

An antimicrobial composition for topical use or for incorporation into a coating or structural composition comprises an antimicrobial silver compound, preferably silver chloride, deposited on a physiologically inert oxidic synthetic particulate support material. A preferred support material is titania containing one or more of the crystalline forms anatase, rutile, and brookite.

8 Claims, No Drawings

ANTIMICROBIAL COMPOSITIONS

This application is a continuation-in-part of Ser. No. 07/068,365 filed Jul. 1, 1987, and now U.S. Pat. No. 4,906,466.

This invention relates to antimicrobial compositions suitable for application to or impregnation in medical and other appliances, for incorporation into a coating or impregnating formulation for such appliances or for topical application.

Medical appliances which may advantageously be coated, impregnated with or manufactured from an antimicrobial composition include catheters, wires, shunts, cannulae, enteral feeding tubes, endotracheal tubes, percutaneous devices, endoprosthetic implants, orthopaedic pins, dental prostheses, sutures, wound dressings, tubing and other apparatus for use in contact with biological fluids. Other (non-medical) applications include any agricultural, industrial or domestic appliance or surface where the maintenance of sterile or contamination-resistant conditions is required, especially where such surfaces are intended for contact with protein-containing liquids or other biological fluids.

Silver is a known anti-microbial metal and various proposals have in the past been put forward for incorporation of silver in a composition for application to a surface intended for contact with biological fluids, to render the fluid or at least a zone thereof in proximity to the surface resistant to microbial infection. In particular, West German patent no. 3228849 (Fraunhofer) suggests that coatings on medical appliances, especially catheters, can be improved by incorporating at least one substance emitting metal ions in the form of a metal or metal compound together with a substance promoting the emission of metal ions and which does not contain the same metal or metal compound as that which emits metal ions. The emitting substance can be gold, silver or copper, preferably applied by cathode sputtering, and the promoter substance is preferably elementary carbon or titanium. Optionally, an adhesion-promoting layer is present between the appliance and the coating and/or there is provided on the coating a porous layer of a tissue-compatible coating such as elementary carbon or a polymer, particularly a polysiloxane, polyolefin or polyfluorine carbon polymer, the porosity of which coating can regulate the microbicidal effect. A further antimicrobial composition is disclosed in WO 84/01721 (Baxter Travenol Laboratories Inc), according to which an antimicrobial coating composition is prepared by mixing a resin with a compound of physiological, antimicrobial metal, optionally in a solvent. Suitable resins include ABS copolymer, PVC, curable silicones, certain silicone rubbers and polyurethanes, and suitable metals include silver, gold, platinum, copper and zinc. It is also stated that combinations of physiological, anticicrobial metal compounds may be used.

The use of supported silver as a water or other liquid purifier is also well documented. Thus, U.S. Pat. No. 2595290 suggests that polluted water may be subjected to mechanical filtration followed by a combined adsorptive and chemical treatment by passage through a granular mass including granules coated with a bactericide of very low water solubility, such as silver chloride. Suitable granular materials include carbon and siliceous materials such as fine sand, and are required to act merely as carriers and not otherwise to enter into the reaction. U.S. Pat. No. 2,066,271, however, suggests that silver metal can be combined with an active zeolite to provide a bactericidal filter material of enhanced activity compared with silver coated on ordinary inert carriers such as sand, carbon and the like. Yet again, European Patent Application No. 0116865 discloses the incorporation of a composition comprising bactericidal metal ions deposited in certain zeolites into a polymer article, to impart to the article a bactericidal effect without causing any deterioration of the physical properties of the polymer. A further disclosure dealing with the use of metallic silver supported on a particulate carrier of specified hardness, admixed with particles of a less hard filler material, is alleged to release silver ions by mechanical interaction of the particles (U.S. Pat. No. 4,608,247). In summary, there have been many prior proposals concerning the use of silver and other antimicrobial metals on various supports for the purpose of providing a sustained antimicrobial or antibacterial effect over a period of time, such an effect being generally referred to as an oligodynamic effect. However, it has hitherto been difficult to realise a composition which in addition to providing a sufficient oligodynamic antimicrobial effect, even in relatively aggressive environments which either provide ideal conditions for the growth of micro-organisms and/or which tend to deactivate the antimicrobial species, is also non-toxic to mammalian cells and is suitable for formulating as a coating or impregnating composition which combines the sustained antimicrobial effect with desirable physical coating or impregnating properties, such as adhesion, extrudability and the like.

It is a further disadvantage of prior art compositions which include silver compounds that the ionic silver may be unstable in the presence of light or other radiation, with the result that it is reduced to metallic silver with a darkening of colour. This effect applies particularly to silver chloride. Articles coated or impregnated with known antimicrobial compositions which include silver compounds may therefore darken on exposure to light, which is a considerable aesthetic disadvantage, particularly where the article is intended for insertion within the body and a white or substantially white appearance is preferred.

We have now found that an antimicrobial silver compound may be combined with certain physiologically inert materials and that the resulting compositions are suitable for application to or impregnation in medical and other appliances, or for incorporation into coating or impregnating formulations for such appliances, whereby a substainable antimicrobial oligodynamic effect is achieved. Furthermore, certain of such compositions achieve suppression of light instability.

According to the present invention, therefore, an antimicrobial composition comprises a sparingly soluble antimicrobial silver compound deposited on a physiologically inert oxidic synthetic support material in particulate form, the support material having an extended surface area.

The physiologically inert support material is oxidic, that is, comprises either an oxide or a hydroxide or contains a complex oxy-anion species such as phosphate or sulphate. Suitable materials are essentially insoluble and stable in water or aqueous environments and will not form hydrates. By "stable in water or aqueous environments", we mean to distinguish between those compounds which in contact with water form a chemically-bound hydrate on the one hand and those which may absorb water to form an associated aqueous species on the other hand, and to indicate the latter.

The surface area of support materials for use in compositions according to the invention should be extended, that is, should be significantly greater than the nominal geometric surface area. The extended surface area is a function of the micro-, meso- and macro-porosity and pore volume of the material. A material which has an extended surface area is to be distinguished from glassy materials such as sand in that the latter have no porosity and their surface areas are substantially the same as their nominal geometric surface areas.

Synthetic oxidic materials which may be suitable as physiologically inert supports in antimicrobial compositions according to the invention include oxides of titanium, magnesium, aluminium, silicon, cerium, zirconium, hafnium, niobium and tantalum, calcium hydroxyapatite, which is a phosphate, and barium sulphate, in which the oxidic material is stable in water or aqueous environments. For example, considering the case of titanium dioxide, which is a preferred material for use in the present invention, the crystalline forms anatase, rutile and brookite are substantially chemically anhydrous and one or more of these forms is suitable for use in the present invention. Fully hydrated or hydratable oxides of titanium are excluded.

The particle size of support materials for use in the invention is preferably less than 25 microns, more preferably in the range 1–15 microns. In general, we prefer to use smaller size particles, including those in the sub-micron range, commensurate with achieving the desired antimicrobial effect. The morphology is preferably such that the structure is highly open. The materials may comprise approximately spherical clusters of crystallites having large physical voidage therebetween. Surface areas may extend from 1 or 2 $m^2g^{-1}$ up to approximately 240 $m^2g^{-1}$, preferably in the range 5–100 $m^2g^{-1}$.

The antimicrobial silver compound is preferably one which is sparingly soluble in aqueous media and in which the silver is present as an ionic species. The form of the compound should, it is believed, therefore be such that release of ionic silver in solution at an effective level for antimicrobial but non-toxic effect is facilitated. Suitable silver compounds are silver chloride, phosphate, hydroxide, carbonate, bromide, acetate, citrate, iodide, lactate, salicylate and stearate, and mixtures thereof with one another or with other silver compounds. It is also believed that interaction between the antimicrobial compound and the support material may lead to stabilisation of the compound in a way which enables the oligodynamic effect to be realised and which may also contribute to suppression of light instability. For example, where the antimicrobial compound is silver chloride and the support is titanium dioxide, titanium dioxide has a tendency to non-stoichiometry such that there may be vacant oxygen bonding sites which leave the crystal lattice with a net slightly positive charge; this in turn may tend to modify the Ag-Cl bond, thereby facilitating release of an ionic silver species in solution, while at the same time stabilizing the silver compound, and thereby suppressing the tendency to reduce to silver metal with resulting darkening of colour, while still present on the support material. Expressed alternatively, the oligodynamic effect is believed to be regulated by the solubility of the antimicrobial compound in the contacting fluid, the support acting to facilitate the supply of an ionic silver species for dissolution while at the same time stabilizing the silver as compound before dissolution. This mechanism is to be contrasted with that of other oxidic supports and in particular with zeolite supports, in that the latter release antimicrobial metal ions by an ion exchange mechanism.

As mentioned above, silver compounds may be used in admixture one with another, possibly co-deposited on the support or by mixing or blending different compositions according to the invention. Accordingly, materials having particularly desirable silver release characteristics may be obtained, or a desired shade may be obtained by deposition on a material or by admixture. For example, it may be desirable to use a mixture of silver iodide with silver chloride or silver phosphate.

The antimicrobial silver compound may be present at a level of from 1–75% by weight of the support material and silver compound, preferably 10–60% by weight. Higher amounts are to be preferred where the composition is to be overcoated with a polymeric material.

A preferred antimicrobial composition according to the invention comprises silver chloride deposited on titania, the silver chloride being present in an amount of, for example, 15%, 20% or 25% by weight of the titania and silver chloride. Such compositions are antimicrobially effective and in addition are suppressive of light instability. An alternative silver compound is silver phosphate, although the light instability suppression is not so marked, at least in normal daylight.

In use, compositions according to the invention may be used topically either as such or incorporated into a suitable formulation for topical application, for impregnation of fibrous or absorbent substrates such as bandages or wound dressings or may be incorporated into coating or impregnating formulations for medical or other appliances. Such formulations generally include a polymeric material, which may be a carbon-based or silicon-based polymer, or based on both carbon and silicon, selected according to the intended use, the method of manufacture of application to be employed, and the degree to which it is required to maintain antimicrobial activity on or in the article or appliance to which the composition is to be applied.

Compositions according to the invention may be applied as coatings or films to appliance substrates by known techniques, including spraying, dipping and extrusion, and may optionally be applied in combination with other polymers or materials or be overcoated with other polymers or materials, for example to improve the smoothness of the surface. Alternatively, the inventive compositions may be used in the manufacture of appliances.

We believe that the antimicrobial silver compounds may be deposited on the particulate support material under conditions of controlled nucleation and growth so that, in those support materials which have large physical voidage, such as titania, the deposited phase is contained largely within the voids, thereby substantially avoiding coalescence of either the antimicrobial silver compound or the support and maintaining the original particle size distribution of the support. We believe that compositions thus produced are suitable for dispersing in a formulation for application to an appliance substrate, and that the resulting coating will remain adhesive on a distensible or otherwise flexible substrate.

Compositions according to the invention may be modified by the inclusion of other ingredients, such as thickeners, opacifiers, co-fillers, levelling agents, surfactants, and dispersion aids.

Antimicrobial compositions according to the invention may be incorporated in polymeric materials is an amount of from 5–60% by weight of the polymer-containing composition, and the resulting compositions may, after application to or embodiment as an appliance, optionally be further coated with a polymeric material or composition.

Exemplary compositions (not overcoated) include the following:

5% $AgCl/TiO_2$* at 40–55% in polymer
15% $AgCl/TiO_2$* at 15–40% in polymer
20% $AgCl/TiO_2$* at 15–49% in polymer
30% $AgCl/TiO_2$* at 15–25% in polymer
60% $AgCl/TiO_2$* at 5–15% in polymer
* Percentages are on the basis of $AgCl/(TiO_2+AgCl)$ The invention also includes, therefore, an antimicrobial coating or structural composition comprising an antimicrobial silver compound deposited on a physiologically inert oxidic synthetic support material in particulate form and having an extended surface area, the composition being dispersed in a polymeric material. Preferably, the polymeric material is biologically compatible, that is, is inert in contact with body or other biological fluids and does not cause a toxic reaction in vivo. In a further aspect, the invention includes a method for reducing the level of micro-organisms in a zone of biological fluid in proximity to a surface, the method comprising applying to the surface an antimicrobial composition comprising a silver compound deposited on a physiologically inert oxidic synthetic support material having an extended surface area, and bringing the treated surface into contact with the said biological fluid. Optionally, the antimicrobial composition is dispersed in a polymeric material which may be a part of or constitute the said surface. By "biological fluid" we mean any aqueous environment in the free liquid or liquid-containing form, whether internal or external to a living system, and containing protein or other substances which would generally be expected to promote the growth of micro-organisms.

Antimicrobial compositions according to the invention may be made by forming a slurry of the support material in an aqueous solution of a salt or other soluble compound of silver and reacting with a compound containing the anion of the desired antimicrobial compound. For example, titania may be slurried in an aqueous solution of silver nitrate and reacted with sodium chloride to precipitate silver chloride on the titania.

The invention will now be described by way of example with reference to experimental results, which illustrate inter alia the antimicrobial effectiveness of compositions according to the invention compared with known compositions, and the suppression of light instability shown by various compositions according to the invention.

PRELIMINARY BACTERIOLOGICAL TESTING

Initial bacteriological testing was carried out in a standard agar plate test using a minimal agar composition, in which the zone size in mm gives an indication of the bacteriological effect. Test compositions were incorporated into silicone based coatings on silicone tube at a loading (for comparative testing purposes) at 25% by weight of the coating, the compositions marked "*" containing equivalent molar amounts of silver, as metal or compound. The percentage compositions given are calculated as Ag or Ag compound/(support + Ag or Ag compound).

The following results were obtained:

| Composition | Zone size (mm) |
| --- | --- |
| * 15% Ag/C (comparative) | 12 |
| * 20% AgCl/C (comparative) | 22 |
| * 20% $AgCl/TiO_2$ | 26 |
| * 15% Ag/C - overcoated with silicone (comparative) | 0 |
| * 20% $AgCl/TiO_2$ | 24 |
| * 20% $AgCl/TiO_2$ - overcoated with silicone | 10 |
| 60% $AgCl/TiO_2$ | 23 |
| 30% $AgCl/TiO_2$ | 23 |
| * 20% $AgCl/TiO_2$ | 22–30 |
| 15% $AgCl/TiO_2$ | 20 |
| 5% $AgCl/TiO_2$ | 10 |
| 50% $Ag/TiO_2$ (comparative) | 14 |
| * $Ag_2SO_4/TiO_2$ | 29 |
| * $Ag_3PO_4$ (comparative) | 28 |
| * $Ag_3PO_4/TiO_2$ | 24–28 |
| 2.5% $Ag/SiO_2$ | 0 |
| 5% $AgCl/SiO_2$ | 15 |
| * 20% $AgCl/SiO_2$ | 29 |

The above results give an indication that compositions according to the invention are at least as effective as prior art compositions containing an equivalent amount of silver and in most cases are superior. In particular, the silicone overcoating on $AgCl/TiO_2$ did not totally mask the antimicrobial effect, as was the case with Ag/C.

TOXICITY

Toxicity testing was carried out on compositions according to the invention and consisting of silver chloride on titanium dioxide dispersed in a silicone coating. Toxicity was measured against HeLa cells and results were obtained as in the following Table:

| | | Composition in coating - % | | | | |
| --- | --- | --- | --- | --- | --- | --- |
| | | 5 | 15 | 25 | 40 | 55 |
| AgCl in | 5 | NT(0) | NT(0) | NT(9) | NT(16) | T(23) |
| composition* | 15 | NT(10) | B (15) | B (20) | T (28) | T(31) |
| % | 20 | NT(16) | NT(25) | B (25) | T (28) | T(31) |
| | 30 | NT(19) | NT(23) | T (29) | T (24) | T(25) |
| | 60 | NT(19) | T (23) | T (24) | T (24) | T(25) |

*These percentages are calculated as $AgCl/(TiO_2 + AgCl)$

In the above table, NT indicates non-toxicity, B indicates borderline and T indicates toxicity. Figures in brackets indicate zone size (mm) on bacteriological testing, as above, against *S.aureus*.

LONG TERM SILVER RELEASE

The long term release of Ag from a composition according to the invention and coated on a silicone catheter was evaluated as follows.

Samples of a 24 FR gauge silicone catheter were coated with a methyl ethyl ketone-suspended coating having the following composition:

125 g room temp. vulcanising silicone rubber
875 g methyl ethyl ketone
83.3 g active phase The active phase contained 15% by weight of AgCl [$AgCl/(AgCl+TiO_2)$] deposited on and in a $TiO_2$ of high purity. The titania had a morphology of a highly open nature, being clusters of acicular crystals of rutile TiO$_2$ with some brookite. The AgCl was deposited by the reaction of AgNO$_3$ with NaCl in a slurry of the TiO$_2$. The concentration of the active phase in the silicone rubber coating composition was 40%.

The coating obtained was adherent, white and evenly distributed. The colour after irradiation sterilisation was still substantially white. 100 mm lengths of catheter were immersed in 9 ml of simulated urine at 37° C. (as per British Standard 1695-1981) and the urine was changed daily. Urine analysis for Ag by Inductively Coupled Plasma showed that a sustained release of ionic silver species could be produced for over 100 days at a level of 2.5 p.p.m.

Bacteriological testing following the above urine immersion gave the following results, where the figures indicate zone size (mm) against S. aureus in standard agar medium.

| Days immersed | Zone size |
| --- | --- |
| 0 | 28,29 |
| 10 | 27,26 |
| 30 | 26,29 |
| 88 | 25,24 |
| 121 | 20,21 |

The coated catheter tube was determined to be non toxic according to the procedures laid down in Australian Standard 2696-1984, standard on the toxicity testing of catheters.

The contents of the said Standards are herein incorporated by reference.

The following Table gives toxicological and bacteriological data for a range of AgCl on TiO$_2$ (rutile+brookite) ratios, dispersed in silicone polymer at various ratios. Toxicological tests were carried out according to the said Australian Standard 2696-1984, according to which any figure greater than 30 indicates non-toxicity. Bacteriological tests were conducted in Iso-Sensitest agar against E.coli NCTC 10418 and S.aureus NCTC 6571 and the figures relate to zone size in mm.

| AgCl / (AgCl + TiO$_2$) (%) | Composition: polymer ratio | | | | | |
| --- | --- | --- | --- | --- | --- | --- |
| | 25:75 | | | 40:60 | | |
| | Tox. | E.coli | S.aureus | Tox. | E.coli | S.aureus |
| 5 | 50 | 0,0 | 0,0 | 75 | 0,0 | 0,0 |
| 15 | 50 | 7,10 | 8,8 | 50 | 13,12 | 12,11 |
| 20 | 50 | 7,7 | 8,7 | 50 | 12,12 | 11,12 |
| 30 | 50 | 10,10 | 10,12 | 50 | 11,12 | 10,10 |
| 50 | 25 | 10,10 | 10,10 | 25 | 12,13 | 12,12 |

IN VITRO ROLLING CULTURE EXPERIMENTS

Samples of silicone rubber tubing were coated with compositions according to the invention as in the preliminary bacteriological tests, the active phase containing 20% by weight AgCl and dispersed in room temperature curing silicone rubber at 40% of the total composition. Freshly prepared and aged active phase were compared; also coating thickness (by reduced solvent content) and dispersing solvents (methyl ethyl ketone (MEK) and methyl isobutyl ketone (MIBK). All samples were white and adherent and remained so on sterilisation. The titania used was as in the long term silver release experiments. Samples of tubing of length 1 cm, were incubated by intermittently rolling for 48 hours in 1.5 ml of Iso-Sensitest broth (Oxoid) at 36° C. (±1° C.) following inoculation with various levels of E.coli NCTC 10418. The growth of bacteria was assessed and the results demonstrate a good antimicrobial effect against a heavy microbial challenge. Results were as follows:

| Composition | Inoculum level per ml | | |
| --- | --- | --- | --- |
| | 1.3 × 10$^3$ | 1.3 × 10$^5$ | 1.3 × 10$^7$ |
| 1. Aged: 20% in MEK | — | — | +/− |
| 2. Aged: 12.5% in MEK | — | — | + |
| 3. Fresh: 20% in MEK | — | — | + |
| 4. Fresh: 12.5% in MEK | — | — | — |
| 5. Fresh: 20% in MIBK | — | — | — |
| 6. Fresh: 12.5% in MIBK | — | — | — |

In the above Table, "−" indicates no bacteria growth and "+" indicates growth. "+/−" indicates reduced growth. The results were verified by growth, sterility and active control tests.

Similarly-prepared samples were also tested by a standard plate zone test with incubation at 37° C. in Iso-Sensitest agar (Oxoid) medium versus both S.aureus and E.coli. The following results represent the mean zone sizes in mm obtained from a number of replicate determinations:

| Composition | Zone size | |
| --- | --- | --- |
| | S.aureus | E.coli |
| 1 | 13.7 | 13.4 |
| 2 | 10.9 | 11.5 |
| 3 | 10.8 | 11.7 |
| 4 | 11.3 | 12.8 |
| 5 | 12.2 | 14.0 |
| 6 | 13.7 | 14.3 |

Similar results were obtained in Meuller-Hinton agar (Oxoid).

Bacteriological tests were also carried out on further compositions according to the invention and containing different silver compounds. Duplicate experiments for each compound were carried out in Mueller-Hinton agar inoculated with S.aureus according to the above standard plate zone test- Results were as follows:

| Composition [Silver compound/(support + silver compound)] | | Zone size (mm) |
| --- | --- | --- |
| 20% AgBr/TiO$_2$ | @ 40% in silicone | 9,9 |
| 20% Ag$_2$CO$_3$/TiO$_2$ | @ 40% in silicone | 12,11 |
| 50% Ag$_2$CO$_3$/TiO$_2$ | @ 40% in silicone | 14,14 |
| 50% AgOH/TiO$_2$ | @ 40% in silicone | 12,13 |
| 20% Ag$_3$PO$_4$/TiO$_2$ | @ 40% in silicone | 13,14 |
| 20% AgCl/TiO$_2$ | @ 55% in silicone | 11,11 |

DYNAMIC LEACH TESTING

Samples of 14 FR gauge silicone tubing coated with a 20% AgCl [AgCl/(AgCl+Support)] antimicrobial composition on titania, alumina and zirconia support materials at 30% in silicone were leached in simulated urine (10 ml per 100 mm tube) at 37° C., thus giving a more stringent test regime than that described above under "long term silver release". Samples were taken initially and after 7 and 13 days' leaching, placed in standard agar medium, inoculated with bacteria (S.aureus), incubated at 37° C. overnight, and the zone size measured. Results were as follows:

| Support | Leach time (days) | Zone size (mm) |
|---|---|---|
| TiO$_2$ | 0 | 30,27 |
| | 7 | 23,23 |
| | 13 | 20,21 |
| Al$_2$O$_3$ | 0 | 30,31 |
| | 7 | 20,20 |
| | 13 | 7,7 |
| ZrO$_2$ | 0 | 22,22 |
| | 7 | 12,15 |
| | 13 | 8,9 |

Similar results were obtained against *E.coli*.

SUPPRESSION OF RADIATION INSTABILITY

Compositions according to the invention and containing AgCl deposited on various support materials were subjected to reflectance spectroscopy using an SP8-200 spectrometer versus PTFE (polytetrafluoroethylene) standard. Measurements were carried out before and after irradiation at 2.5 Mrad of gamma radiation. The following data represent % reflectance at the indicated wavelengths.

| Support Material | Wavelength (nm) | | | | | |
|---|---|---|---|---|---|---|
| | 300 | 400 | 500 | 600 | 700 | 800 |
| TiO$_2$ - substrate only | 4 | 30 | 98 | 99 | 99 | 99 |
| TiO$_2$ - unirradiated | 4 | 30 | 93 | 94 | 94 | 95 |
| TiO$_2$ - irradiated | 4 | 30 | 79 | 76 | 76 | 76 |
| Al$_2$O$_3$ - irradiated | 45 | 71 | 69 | 66 | 65 | 64 |
| ZrO$_2$ - irradiated | 40 | 72 | 71 | 66 | 64 | 62 |

Radiation-sensitive prior art compositions are visibly inferior than those compositions tested above.

We have also carried out physical and other characterisation tests of potential support materials, in an attempt to establish the nature of any interaction between the material and a deposited antimicrobial compound. Tests carried out have included analysis by X-ray photoelectron spectroscopy, scanning electron micrographs, zero point of charge, temperature programmed reduction, surface area, pore size distribution, secondary ion mass spectrometry, particle size analysis, X-ray diffraction and chemical analysis.

We claim:

1. A finely divided, particulate antimicrobial composition comprising a sparingly soluble antimicrobial silver compound deposited on a finely divided particulate support consisting essentially of an oxidic material which is stable in water or aqueous environments and is selected from the group consisting of oxides of titanium, magnesium, aluminum, silicon, cerium, zirconium, hafnium, niobium and tantalum, and barium sulphate said support being one which does not form hydrates, and has an extended surface area.

2. A composition according to claim 1, in which the support material comprises titania containing one or more of the crystalline forms anatase, rutile and brookite.

3. A composition according to any preceding claim, in which the support material has a particle size less than 25 microns.

4. A composition according to claim 1, in which the surface area of the support is in the range 1-240 m$^2$g$^{-1}$.

5. A composition according to claim 1, in which the silver compound has a low solubility in aqueous media and in which the silver is present as an ionic species.

6. A composition according to claim 1, in which the silver compound is present at a level of from 1-75% by weight of the support material plus silver compound.

7. A composition according to claim 6, in which the silver compound comprises silver chloride.

8. A method for reducing the level of microorganisms in a zone of biological fluid in proximity to a surface, the method comprising applying to the surface a finely divided particulate antimicrobial composition comprising a sparingly soluble antimicrobial silver compound deposited on a finely divided particulate support material consisting essentially of an oxidic material which is stable in water or aqueous environments and is selected from the group consisting of oxides of titanium, magnesium, aluminum, silicon, cerium, zirconium, hafnium, niobium and tantalum and barium sulphate, said support being one which does not form hydrates, and has an extended surface area.

* * * * *